(12) United States Patent
Lauer

(10) Patent No.: US 9,999,736 B2
(45) Date of Patent: Jun. 19, 2018

(54) DEVICE AND EXTERNAL FUNCTIONAL MEANS AND TREATMENT APPARATUS FOR THE TREATMENT OF MEDICAL FLUIDS

(75) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 456 days.

(21) Appl. No.: 12/766,098

(22) Filed: Apr. 23, 2010

(65) Prior Publication Data

US 2010/0270222 A1 Oct. 28, 2010

Related U.S. Application Data

(60) Provisional application No. 61/185,604, filed on Jun. 10, 2009.

(30) Foreign Application Priority Data

Apr. 23, 2009 (DE) .................... 10 2009 018 664
Jun. 10, 2009 (DE) .................... 10 2009 024 467

(51) Int. Cl.
| | |
|---|---|
| *B01D 29/13* | (2006.01) |
| *B01D 69/10* | (2006.01) |
| *A61M 5/38* | (2006.01) |
| *A61M 5/165* | (2006.01) |
| *B01D 19/00* | (2006.01) |

(Continued)

(52) U.S. Cl.
CPC ............ *A61M 5/385* (2013.01); *A61M 5/165* (2013.01); *A61M 1/0084* (2013.01); *A61M 2205/125* (2013.01); *B01D 19/0031* (2013.01); *B01D 36/001* (2013.01)

(58) Field of Classification Search
CPC .. A61M 1/0001; A61M 1/3627; A61M 27/00; A61M 1/16; A61M 1/0023; A61M 2001/0092; A61M 2205/123; A61M 1/0005; A61M 2001/0015; A61M 2001/0017; A61M 2001/0052; A61M 5/385
USPC .... 210/650, 104, 136, 257.2, 258, 259, 314, 210/321.6, 406; 604/305, 313, 319, 320, (Continued)

(56) References Cited

U.S. PATENT DOCUMENTS

| | | | |
|---|---|---|---|
| 2,775,240 A | * 12/1956 | Morrisey, Jr. et al. | ........ 604/405 |
| 3,631,654 A | * 1/1972 | Riely et al. | ........................ 96/6 |

(Continued)

FOREIGN PATENT DOCUMENTS

| | | |
|---|---|---|
| DE | 3316043 A1 | 11/1984 |
| DE | 197 33 407 A1 | 2/1999 |

(Continued)

OTHER PUBLICATIONS http://www.carl-roth.de/catalogue, Carl Roth GmbH website.
(Continued)

*Primary Examiner* — Pranav N Patel
(74) *Attorney, Agent, or Firm* — Fish & Richardson P.C.

(57) ABSTRACT

The present invention relates to a device comprising at least one fluid reception chamber and at least one hydrophobic filter means, wherein a vertical through the hydrophobic filter means does not have a point of intersection with a fluid level of fluids present in the fluid reception chamber. It further relates to an external functional means as well as a treatment apparatus.

35 Claims, 3 Drawing Sheets

(51) Int. Cl.
*B01D 36/00* (2006.01)
*A61M 1/00* (2006.01)

(58) Field of Classification Search
USPC ....... 604/306, 315, 317, 318, 321, 322, 324, 604/403, 405, 406, 408, 409, 410
See application file for complete search history.

(56) References Cited

U.S. PATENT DOCUMENTS

| | | | |
|---|---|---|---|
| 4,177,149 A * | 12/1979 | Rosenberg | 210/436 |
| 4,475,914 A * | 10/1984 | Portnoff | 604/414 |
| 4,529,419 A | 7/1985 | Perl et al. | |
| 4,826,494 A * | 5/1989 | Richmond et al. | 604/323 |
| 5,005,198 A | 4/1991 | Toda | |
| 5,055,198 A * | 10/1991 | Shettigar | 210/650 |
| 5,244,930 A | 9/1993 | Trudell et al. | |
| 5,496,299 A | 3/1996 | Felix et al. | |
| 5,662,642 A * | 9/1997 | Isono et al. | 604/403 |
| 5,669,892 A * | 9/1997 | Keogh et al. | 604/320 |
| 5,707,520 A * | 1/1998 | Kuroki et al. | 210/436 |
| 5,827,429 A * | 10/1998 | Ruschke et al. | 210/321.75 |
| 5,941,866 A * | 8/1999 | Niedospial, Jr. | A61J 1/10 604/403 |
| 6,251,291 B1 * | 6/2001 | Lamphere et al. | 210/767 |
| 6,508,859 B1 * | 1/2003 | Zia et al. | 95/46 |
| 6,702,941 B1 * | 3/2004 | Haq | B01D 46/0013 210/315 |
| 7,322,969 B2 * | 1/2008 | Hattori et al. | 210/257.1 |
| 7,429,325 B2 * | 9/2008 | Ingvarsson | 210/257.1 |
| 2002/0115980 A1 * | 8/2002 | Niedospial et al. | 604/411 |
| 2002/0161317 A1 | 10/2002 | Risk et al. | |
| 2002/0183702 A1 | 12/2002 | Henley et al. | |
| 2003/0120202 A1 * | 6/2003 | Gordon | 604/28 |
| 2004/0226444 A1 * | 11/2004 | Leahey | 96/6 |
| 2006/0015087 A1 * | 1/2006 | Risk et al. | 604/541 |
| 2008/0045919 A1 * | 2/2008 | Jakob et al. | 604/406 |
| 2010/0133153 A1 | 6/2010 | Beden et al. | |

FOREIGN PATENT DOCUMENTS

| | | |
|---|---|---|
| DE | 102 24 750 A1 | 12/2003 |
| DE | 10 2009 012632.5 A1 | 9/2010 |
| DE | 10 2009 018664.6 A1 | 9/2010 |
| DE | 10 2009 024468.9 A1 | 9/2010 |
| EP | 1960020 A1 | 8/2008 |
| EP | 2260890 A1 | 12/2010 |
| EP | 2263726 A2 | 12/2010 |
| JP | S-62-500913 A | 4/1987 |
| JP | 2799179 B2 | 9/1998 |
| JP | 2002-063470 A | 2/2002 |
| JP | 2002527212 A | 8/2002 |
| JP | 2003520072 | 7/2003 |
| JP | 2005103256 A | 4/2005 |
| JP | 2005528168 | 9/2005 |
| JP | 2005-531340 A | 10/2005 |
| JP | 2006-142192 A | 6/2006 |
| JP | 2011-031908 A | 2/2011 |
| JP | 2010-080602 A | 10/2011 |
| JP | S51-008569 U | 12/2012 |
| WO | 9521644 A1 | 8/1995 |
| WO | 0023140 A1 | 4/2000 |
| WO | 01/37922 A2 | 5/2001 |
| WO | 03101508 | 12/2003 |
| WO | 2004/039439 A2 | 5/2004 |

OTHER PUBLICATIONS

Japanese Search Report by Registered Searching Organization in Japanese Application No. 2012-506376, dated Jan. 24, 2014, 54 pages (with English translation).

Japanese Search Report by Registered Searching Organization in Japanese Application No. 2015-004187, dated Nov. 27, 2015, 46 pages (with English translation).

* cited by examiner

DEVICE AND EXTERNAL FUNCTIONAL MEANS AND TREATMENT APPARATUS FOR THE TREATMENT OF MEDICAL FLUIDS

RELATED APPLICATIONS

This application claims the benefit of U.S. Provisional Patent Application No. 61/185,604, filed on Jun. 10, 2009, which is expressly incorporated herein in its entirety by reference thereto. Further, this application claims priority to German Patent Application No. 10 2009 018 664.6, filed on Apr. 23, 2009, and German Patent Application No. 10 2009 024 467.0, filed on Jun. 10, 2009, each of which is expressly incorporated herein in its entirety by reference thereto.

FIELD OF THE INVENTION

The present invention relates to a device having at least one fluid reception chamber for receiving at least one first medical fluid, in particular blood, and at least one hydrophobic filter means having a filter surface through which at least one second gaseous fluid, in particular air, may be supplied to the fluid reception chamber. It further relates to an external functional means for treating at least one fluid, as well as a treatment apparatus for treating at least one fluid.

BACKGROUND

Various treatment apparatuses such as in medical technology, comprise devices wherein fluids are to be treated or to be stored temporarily.

It is an object of the present invention to specify another device that is suited for this purpose.

SUMMARY

In all of the following explanations, the usage of the expression "may be/have" should be understood to be synonymous with "preferably is/has."

The device of the invention comprises at least one fluid reception chamber suited and adapted for receiving at least one first medical fluid. It further comprises at least one hydrophobic filter means for feeding or supplying a second, gaseous fluid into an interior of the fluid reception chamber.

The expression "fluid reception chamber" as presently used designates a chamber or a container having an interior or an inner space which is suited and, according to its purpose of use, intended for being completely or partly filled with fluids and receiving the latter.

A "first fluid" within the meaning of the present invention includes any medical liquid and/or any medical gas as well as arbitrary combinations thereof envisioned or intended for introduction into a reception means in accordance with the invention. In a preferred manner or configuration, the first fluid is blood.

The expression "first fluid" shall therefore be used synonymously with the expression "medical fluid."

A "second fluid" is a gaseous fluid, preferably air.

The expression "filter means" or "hydrophobic filter means", as used synonymously in the present application, designates a means adapted and intended to exert a filter effect on fluids that are to be conducted through the fluid reception chamber. Alternatively, a filter means within the meaning of the invention may designate a membrane not having a filter effect.

The filter effect may encompass, e.g., a purification of the fluids being fed or supplied into the fluid reception chamber, in particular, for instance, retaining of solids, micro-organisms such as viruses or bacteria, and the like.

In accordance with the invention, the filter means is arranged such that a normal vector on the filter surface of the hydrophobic filter means does not extend in parallel with a normal vector on the plane of the fluid level of the first fluid present in the fluid reception chamber. In other words, the two normal vectors are not present in one plane.

The expression "normal vector" as presently used in relation to the filter surface designates a normal vector relative to an arbitrary surface portion or section or segment of the filter means. The normal vector on the filter surface may be a line perpendicular to a plane of main extension of the filter means, in a particularly preferred manner a line perpendicular to a surface of a main portion of the filter means, and in a quite particularly preferred manner a line perpendicular to a central portion of the filter means or a line perpendicular to a filtering portion of the filter means or of the non-filtering membrane. Such a normal vector on the filter surface may represent a vertical plumb or a line perpendicular to one of the afore-mentioned portions.

The expression "normal vector on the plane of the fluid level" as presently used—in analogy with the definition for the normal vector on the filter surface as given in the foregoing—designates a normal vector relative to an arbitrary portion or segment or region of the plane of the fluid level.

In accordance with the invention, the expression "fluid surface" relates to a fluid surface or level (these two expressions shall in the following be used synonymously) of a first fluid present in the fluid reception chamber.

The fluid level is limited to an interior of the fluid reception chamber. It does not exceed outside the fluid reception chamber. The fluid level is preferably not understood to be the entire plane drawn through the fluid level but only the region of this plane inside the fluid reception chamber that is limited by walls or other structures.

The fluid level is preferably limited to an area of contact or a contacting portion of the first fluid with a second fluid equally present inside the fluid reception chamber. Preferably, the fluid level does not extend beyond this. The fluid level thus is preferably only present inside the fluid reception chamber.

In the event of hunting or sloshing, respectively, and/or flow movements, such as, for example rotating and/or undulating movements of the fluids present in the fluid reception chamber, it may be difficult to draw and determine a fluid level or an perpendicular line thereon, respectively. Accordingly, in terms of the invention, a fluid level is preferably understood to be an average level or filling height averaged under consideration of any sloshing and/or flow movements of the fluids present in the fluid reception chamber.

The fluid level may preferably be determined in a resting state of flow of the fluid or in static fluid conditions. It is insignificant whether such a resting state is obtained during use of the device. For the present purposes it is sufficient to assume or approximate such a resting state.

In a preferred embodiment, the normal vector on the filter surface is substantially perpendicular to the normal vector on the plane of the fluid level.

The expression "substantially perpendicular" as presently used encompasses deviations from right angles owing, e.g., to the fact that the external functional means—for instance a blood treatment cassette—comprising the device of the invention exhibits a slight inclination during use, e.g. up to +/−15 degrees, whereas the fluid or liquid level in the external functional means nevertheless remains horizontal at such an inclination of the filter means.

In another preferred embodiment of the invention, a normal vector on the filter surface does not have a point of intersection with a fluid level—as defined in the foregoing—of the first fluid present in the fluid reception chamber.

In a preferred embodiment in accordance with the invention, the device comprises at least one fluid supply chamber for supplying the second fluid.

The expression "fluid supply chamber" as presently used designates a chamber or a container having an interior or inner space suited and intended for receiving a second fluid and supplying it into the fluid reception chamber.

The fluid supply chamber may be manufactured as an injection-molded chamber. The fluid supply chamber may be a single-use fluid supply chamber.

The fluid supply chamber may be connected to the fluid reception chamber in at least one portion thereof.

The fluid supply chamber may be connected to the fluid reception chamber by material connection or may be integrated therewith.

The fluid supply chamber may be realized, for example, during manufacture of the fluid reception chamber.

The fluid supply chamber may be separated from the fluid reception chamber by at least one partition or partial wall.

In another preferred embodiment of the present invention, the filter means is disposed in an interior of the fluid supply chamber.

In a preferred manner, the fluid supply chamber and the fluid reception chamber are in fluid communication with each other via the filter means alone. The second fluid is preferably introduced or supplied or fed from the fluid supply chamber through the filter means into the fluid reception chamber.

In a particularly preferred manner, the filter means is configured and provided such that a first fluid present in the fluid reception chamber cannot enter the fluid supply chamber through the filter means.

To this end, the second fluid to be supplied to the fluid reception chamber may pass or flow through the filter means. In a preferred manner, it is advantageously cleansed or purified from undesirable solids, undesirable fluids, bacteria, and the like in or by the filter means. In this way, the introduction or entrainment of undesirable substances from an exterior of the device into the fluid reception chamber may advantageously be prevented. In addition, a spread or dissemination thereof starting from the fluid reception chamber may also advantageously be avoided.

The second fluid may be supplied, made to flow, introduced, etc. into the fluid supply chamber via a fluid connector which is connectable, or connected, to the fluid supply chamber.

The fluid connector may be a sleeve-type construction. It may be manufactured integrally with a wall or side wall of the fluid supply chamber. It may be provided on or at an outer face of the wall or side wall of the fluid supply chamber. It may be provided inside a region of the filter means disposed in the fluid supply chamber. It may be directly connected or coupled to the filter means.

The fluid connector may be connected to an inside of the wall or side wall of the fluid supply chamber through the intermediary of one or several connecting bores.

In each embodiment in accordance with the invention, the fluid reception chamber may, for example, be manufactured in the form of an injection-molded chamber.

The fluid reception chamber may be a single-use fluid reception chamber.

The fluid reception chamber may be in a fluid connection with an outside of the chamber. The fluid reception chamber may have two or more fluid connections with the outside of the chamber.

In another preferred embodiment, the filter means comprises at least one filter membrane.

A "filter membrane" is preferably adapted and intended to filter undesirable foreign matter and the like from the second fluid being supplied to the fluid reception chamber. In accordance with the invention, however, a filtering function is not an indispensable or mandatory property of the membrane. The filter membrane possesses customary properties that are well-known for a membrane.

By means of the filter membrane, the fluid reception chamber is preferably uncoupled from the fluid connector of the fluid supply chamber and/or from an outside of the device.

The filter membrane may have any suitable shape. It may be configured, for example, to be round, polygonal, in particular rectangular, elliptical, and the like.

The filter membrane may be cut out from a filter membrane ribbon and/or may—in a given case—be cut to a particular shape.

The filter membrane may be a single-use filter membrane.

The filter membrane may be a hydrophobic membrane. The filter membrane may be hydrophobic on at least one side.

The filter membrane may consist of two layers, i.e., firstly the proper membrane itself mostly consisting of a material that is difficult to weld and difficult to bond such as, e.g., PTFE (polytetrafluoroethylene), and secondly a layer having drainage and/or support function and mostly consisting of a woven and/or nonwoven material capable of being welded and/or bonded. Apart from the aforementioned layers, the filter membrane may alternatively comprise additional layers or components.

The filter membrane may be a sterile membrane.

The filter membrane may be comprised of, or include, a material which is not, or only poorly, suited for bonding, and/or a material which is not, or only poorly, suited for welding.

The filter membrane may be connected to or integrated with the fluid supply chamber by material connection (e.g., by welding and/or bonding) and/or frictional connection (e.g., by pressing with an O-ring) and/or by form closure connection.

During use of the device such as, for example, during the duration of a treatment, the filter membrane may be exposed to varying pressures imposed by the fluid reception chamber (outflowing gas, accumulated liquid) and/or from the direction of a treatment apparatus (inflowing gas, accumulated liquid in fault case and/or undesirable liquid resulting from condensation). As a protection of the filter membrane in the planar area of utilization and/or at its locations of sealing (generally welding), e.g., on walls of the fluid supply chamber, against a deformation by these pressure differences which might cause a structural damage or a tear in the membrane, a mechanical support of the filter membrane may be advantageous.

In order to achieve such a mechanical support it is possible to employ a support structure. The support structure is configured such that the support surfaces of the filter membrane do not inadmissibly seal against the desired passage of fluid through the filter membrane, e.g., a passage of useful gas.

The filter means may have a symmetrical or an asymmetrical construction.

In a preferred embodiment of the present invention, the filter means comprises a support structure at or on at least one side or both sides.

A first and a second support structure may be provided on both sides of the filter membrane. They may be arranged separately or to be separate from the latter. A third support structure may be arranged on the membrane layer. It may preferably have the form of a nonwoven material, a woven material, or the like.

The first support structure is preferably provided inside the housing of the fluid connector. It may have a drainage structure. The first support structure may convey or impart a drainage effect.

The first support structure may be connected by frictional and/or by form closure and/or by material connection to the fluid supply chamber. In a preferred manner, the first support structure is connected by frictional and/or by form closure and/or by material connection to the fluid supply chamber in an outer peripheral region thereof.

As the filter membrane generally includes a material that is not, or only poorly, suited for bonding and/or not, or only poorly, suited for welding, the support structure facing the interior of the fluid supply chamber may be connected to the fluid supply chamber in at least one outer region, preferably an outer peripheral region thereof.

In a preferred manner, the first support structure is connected to the fluid supply chamber by material connection, for example by means of welding as, e.g., by means of thermal welding. The first support structure may be thermally welded with the fluid supply chamber or to a connecting region thereof.

To this end, the first support structure is—preferably in an outer region thereof—made of a higher-melting point material than the connecting region of the fluid supply chamber.

During welding the first support structure with the fluid supply chamber or a connecting region thereof, the material of the fluid supply chamber liquefied by heating may penetrate into a porous structure of the support structure. The liquid material may penetrate up to the filter membrane. In this way, it is advantageously possible to form a non-releasable connection between the fluid supply chamber, the first support structure, and the filter membrane. At the same time, the filter membrane may advantageously be sealed, in particular in a lateral direction.

The second support structure is preferably a thin-walled injection-molded part. It preferably comprises a drainage structure on the side facing the membrane layer or on both sides.

The first and/or second support structure may be produced by means of injection molding.

For example, the first support structure may be integrated in a wall of the fluid supply chamber manufactured by an injection molding technique.

In another preferred embodiment, the filter membrane comprises a second support structure at or on the side of the filter membrane facing away from the interior of the fluid supply chamber.

The second support structure may be disposed substantially in parallel with the filter membrane.

The second support structure may be provided in non-pressurized contact with the filter membrane and/or with little play on the side of the filter membrane facing away from the interior of the fluid supply chamber.

The second support structure may be made of the same material as the fluid supply chamber.

The second support structure may form, or be manufactured as, a separate element. For instance, the second support structure may be manufactured as a thin-walled injection-molded part.

In a further preferred embodiment, the second support structure covers the filter membrane substantially completely.

The second support structure facing away from the inside of the fluid supply chamber may have its area and/or boundary delimited towards the outside by an ring zone or an ring region which does not have a drainage effect.

The expressions "ring zone" or "ring region" designate an external region or external margin or an external edge or outer margin or outer edge of the second support structure. The word component "ring" is, however, not intended to restrict the invention to a circular configuration of the zone or of the region. It is rather intended to denote a peripheral region or a peripheral zone which may, however, also be configured in any other suitable form, for example in the shape of a rectangle, an ellipse, and the like.

An outer boundary of this ring zone or ring region may substantially correspond to the external dimensions of the filter membrane.

An internal boundary of this ring zone or ring region may substantially correspond to the filter membrane area having a filtering effect which is left after fixation of the filter membrane to the ring zone or ring region.

The filter membrane may be connected to the second support structure in a gas-tight manner. It may be connected to a wall material of the ring zone or ring region. For instance, the filter membrane may be connected in an outer, preferably peripheral, region thereof to the second support structure or to an outer ring region of the latter.

The filter membrane may be connected to the wall material by material connection. It may, for example, be bonded to or welded with the wall material.

The filter membrane may correspondingly be connected to or integrated with both the first support structure and the second support structure.

The second support structure may be a thin-walled injection-molded part or element that is connectable to the filter membrane and/or to the housing of the filter means by means of welding and/or bonding.

A construction of the device of the invention comprising at least three support structures may exemplarily be formed as follows:

The third support layer is applied on the filter membrane. During assembly, the third support layer, e.g. a weldable nonwoven layer, is placed on the first support structure on the side of the nonwoven layer. The third support layer is welded with and/or bonded to the first support structure in a peripherally sealing manner at the circumference of the filter membrane layer, i.e., preferably in the region situated outside the first support structure. In this way, a sealing function between the third support structure and the first support structure may advantageously be achieved.

The second support structure, e.g., a thin-walled injection-molded part, is placed like a lid with its support structure on the filter membrane which is welded to the first support structure. It is welded with and/or bonded to the housing (injection-molded housing) of the fluid connector in an outer ring zone outside the filter membrane layer.

The second support structure advantageously provides a retaining function for the filter membrane.

The first and/or second support structure(s) may be configured such that after arranging the support structure(s) there are still some freely accessible surface parts of the filter membrane present without any support, wherein each of the freely accessible surface parts have a sufficiently small extension to the adjacent mechanical supports or support structures.

In a preferred manner, the maximum admissible fluid pressure of the second fluid acting on the unsupported filter membrane areas thus does not generate an inadmissibly high stress (for instance due to buckling of the filter membrane) any more.

For instance, single ones or all of the support structures such as, for example, drainage structures, may have a width of about 0.5 to 2 mm.

The fluid connector arranged on the outside may communicate via bores, recesses or openings with the outer drainage or support structure, i.e., the first support structure, for the filter membrane.

The filter membrane arranged between the first and second support structures can substantially endure a mechanical load up to such an extent that is required in accordance with the purpose of use.

The plane in which such a membrane connection—i.e., a connection between the filter membrane and the two support structures—is arranged may substantially correspond to the plane in which projected regions of the drainage structure are arranged.

Depending on the connection technique and/or thickness of the filter membrane, a staggered height between projected regions of the drainage structure and the outer-side plane of the filter membrane may be reasonable. Such a staggered height may serve to let the outer-side plane of the filter membrane rest on the projected drainage structures in non-pressurized contact and/or with little play.

The projected drainage structures may be arranged to be as small as possible.

Preferably only a restricted flow of the second fluid may take place through the filter membrane regions that come into contact and/or in pressed contact with the projected drainage structures that rest against them.

The size and/or number of the connecting bores to the fluid connector and/or the arrangement, number, width and/or depth of the recessed drainage structures may be such that a possible pressure drop of the second fluid caused by these flow paths makes up for a negligible or acceptable fraction of the total pressure drop occurring upon passage through the filter means.

The width of the recessed drainage structures and/or the diameters of the connecting bores to the fluid connector may be adapted to be sufficiently small such that the tensile forces acting on the filter membrane under maximum possible pressure differences (resulting, for example, in buckling into the recessed structures) are clearly lower than the admissible tensile forces, preferably both within the filter membrane and in the—generally more sensitive—zones at the interface to the ring fixation (e.g., weld).

In another preferred embodiment, the first and second support structures comprise a drainage structure that is identical in a mirror-reversed manner relative to a main plane of the membrane, or substantially identical.

In a preferred manner, the recessed and/or projected drainage structures oppose each other in a congruous or substantially congruous manner.

In preferred manner, the recessed drainage structures on the one filter membrane side are realized to be narrower, or in turn the projected drainage structures on this side of the filter membrane are realized to be wider than the drainage structures on the other side of the filter membrane. This may allow a greater lateral installation tolerance. The pitches and/or arrangements of the structures may, however, in a preferred manner be realized identically on both sides.

In this way, by making use of the lateral installation tolerances, a very constant property profile concerning properties such as fluid passage resistance and degree of mechanical support may result.

The overall thickness of the structure of the second support structure may result from the depth of the drainage structure and/or from the minimum possible wall thickness of the material of the second support structure, or be the sum thereof. As a result, the second support structure may advantageously require little structural space and/or be manufactured at lower cost.

Another advantage may arise from the fact that there are no particular demands to the second support structure with regard to accuracy and rigidity. It may moreover advantageously be possible to fasten the second support structure at the fluid supply chamber solely under aspects of costs and/or the lowest possible complexity.

As is shown in FIGS. 1 and 2, the second support structure may, for example, be connected to the fluid supply chamber by means of plug-in or riveting fixation or according to the principle of bolt fixation. Likewise, the second support structure may be connected to the fluid supply chamber by means of dot-shaped welds and/or snapping into suitable geometrical configurations of a side wall or wall of the fluid supply chamber.

In one embodiment in accordance with the invention, the drainage structures of the second support structure may, inter alia or solely, differ from the outside drainage structures in that the former do not end at the membrane boundaries at their outside but radially continue up to the component boundary at their outside. Thus, fluids flowing in and/or out may freely penetrate into the remaining annular or ring space between the second support grid and an upper boundary or an upper margin or edge of the fluid supply chamber. The fluids may advantageously communicate with the fluid reception chamber via a large lumen.

In a further preferred embodiment of the present invention, the fluid reception chamber has a first structural height, and the fluid supply chamber has a second structural height different from the first structural height.

Also, or in addition, the fluid supply chamber may be disposed above the fluid reception chamber ("top") during use of the device. "Above" may relate to a reference system as drawn through the center of the Earth.

In such an arrangement of the fluid reception chamber and the fluid supply chamber, the device is preferably embodied with a stepped depth. The deep fluid reception chamber arranged below the fluid supply chamber ("bottom") during use of the device may be utilized as a reservoir and/or treatment space for the fluids present therein during use.

The device of the invention may be configured in a cassette design. It may, for example, be part of an external functional means. The device may, for example, be integrated in the external functional means by material connection.

The external functional means may be provided with a cover member on at least one side.

A "cover member" may, for example, be a membrane, a film, and the like. Exemplary embodiments of suitable cover members as well as their realization and arrangement on the external functional means may, for example, be taken from German Patent Application No. 10 2009 012 632.5 (representative's file FM19A25) to the applicant of the present invention as filed with the German Patent and Trademark Office on Mar. 10, 2009 and having the title "*Abdichtung-*

*seinrichtung zum Abdichten eines Volumens einer medizinischen Behandlungsanordnung gegen ein weiteres Volumen sowie Anordnung and Verfahren*" [A sealing means for sealing a volume of a medical treatment arrangement against another volume, as well as an arrangement and a method], the relevant disclosure of which is herewith fully incorporated by way of reference thereto.

In a particularly preferred manner, the filter means is arranged in parallel or substantially in parallel with the cover member of the external functional means.

The external functional means may be suited and intended for treating the first fluid.

Such a treatment may, for example, be performed by varying the volume and/or the pressure of the first fluid in the fluid reception chamber by filling, emptying and/or application of pressure. To this end, the first fluid in the fluid reception chamber may, for example, be superposed by a volume of the second fluid. The second fluid may, for example, transmit the afore-mentioned functions to the liquid through the intermediary of a connection to a treatment apparatus which may comprise corresponding actors and/or control or regulation means.

In a particularly preferred embodiment of the present invention, the second fluid is a gas. In a further preferred manner, the first fluid may be a liquid such as, for example, blood.

The device of the invention is suited for use in, or on, or with a treatment apparatus such as a medical treatment apparatus, an apparatus used in laboratory technology, an apparatus used in food and/or drug manufacture. Fluids suited for being introduced or supplied or conducted into the reception means in accordance with the invention may therefore encompass both medical liquids such as blood, substitute (e.g., saline solution), preparations of active agents such as solutions, suspensions, emulsions, carrier gases for active agents, cleaning liquids or gases, disinfection liquids or gases, sterilization liquids or gases, beverage liquids, and the like.

When the filter membrane is provided as a sterile membrane, the device of the invention may in particular be utilized for sterile air supply to the fluid reception chamber.

The object of the invention is also achieved through an external functional means according to claim 28. All the advantages of the reception means in accordance with the invention may also be obtained with the external functional means of the invention.

An external functional means of the invention comprises a device in accordance with the invention.

The external functional means of the invention may be envisioned for use in a treatment method. Treatment methods within the meaning of the present invention encompass medical or medical-technical treatment methods, treatment methods of laboratory technology, food or drug manufacture, and the like.

Such an external functional means may be a single-use component or a single-use article manufactured, e.g., of a plastic material.

The external functional means may be manufactured by means of an injection molding technique.

The external functional means may be open at the top.

The external functional means may include liquid and/or gas connections, semi-open passages and/or chambers and/or structures for coupling to actors and/or sensors. Such actors and/or sensors may serve for performing functions preferably non-invasive and/or uncoupled as regards sterility on the liquids in the cassette. One or several cover members such as, for example, membranes, in particular low-cost films, may provide for closure and/or sealing of the passages and chambers.

In a further preferred embodiment, the filter means of the device is arranged in parallel with a cover member of the device for closing an interior of the fluid reception chamber against an outside.

In a preferred embodiment, the external functional means of the invention is configured as a blood cassette.

Such a blood cassette is described, for example, in German Patent Application No. 10 2009 018 664.6 (representative's file FM19A27) as filed with the German Patent and Trademark Office on Apr. 23, 2009 and having the title "*Externe Funktionseinrichtung, Blutbehandlungsvorrichtung zum Aufnehmen einer erfindungsgemäßen externen Funktionseinrichtung, sowie Verfahren*" [External functional means, blood treatment apparatus for receiving an external functional means in accordance with the invention, and method], as well as the German patent application 10 2009 024 468.9 (G09/046; (11)FM19B27) of the same title filed on Jun. 10, 2009, by the applicant of the present invention, the relevant disclosures of which are herewith fully incorporated by way of reference thereto.

The external functional means may be provided for use in or on a treatment apparatus.

The object of the invention is therefore equally achieved through a treatment apparatus as disclosed herein. All the advantages of the device of the invention may also be achieved with the treatment apparatus of the invention.

The treatment apparatus of the invention may comprise a device of the invention and/or an external functional means of the invention.

The treatment apparatus may be utilized in a treatment method as specified in the foregoing.

For instance, the treatment apparatus may be a blood treatment apparatus such as a dialyzing apparatus for performing a dialysis treatment such as a hemodialysis, a hemofiltration, a hemodiafiltration, and the like.

The device of the invention may advantageously be utilized for the sterile air supply of a fluid reception chamber.

The treatment apparatus may comprise at least one reception means suited and intended for receiving at least one blood treatment cassette comprising at least one device of the invention.

In contrast with conventional arrangements for the sterile air supply of external functional means in which the hydrophobic sterile membranes are disposed at the highest point of the fluid reception chamber and substantially in parallel with the free fluid surface, the filter membrane provided in accordance with the invention may preferably be arranged in a geodetic manner above the fluid reception chamber that is normally filled with fluids to the maximum. During failure-free operation, the fluid supply chamber may therefore advantageously only get into contact with the second fluid, for instance gas, and with small quantities of the first fluid, e.g., a liquid such as blood.

As the filter membranes employed in accordance with the invention are sensitive elements and difficult to examine and should therefore generally be replaced for every treatment utilization, the filter membrane may advantageously be a component of the single-use functional means. Such filter membranes may moreover in a further advantageous manner be sterilized in combination with the single-use functional means and/or keep the single-use partial system closed in a sterile manner during storage and/or during connecting to the treatment apparatus.

Hydrophobic filter membranes may furthermore advantageously ensure that the fluids to be treated which are present in the fluid reception chamber are prevented from entering the treatment apparatus in the event of malfunction.

The device of the invention may advantageously utilize the spatial and/or functional arrangements present in single-use functional means frequently provided for treatment apparatuses, in particular blood treatment apparatuses, for accommodation, for pressing, for compensating tolerances, for limiting forces, for mounting, for orientation and/or for handling in parallel with other functional units of the overall arrangement.

The different geometrical environmental conditions of conventional arrangements together with the arrangement of the fluid supply chamber and of the fluid reception chamber of the device in accordance with the invention may advantageously result in a higher gas pressure loss per area unit at the drainage or support structures due to confined space in the surroundings of the filter membrane. In this way, it may advantageously be possible to employ more cost-efficient and smaller-structured filter membranes at an identical pressure loss, so that it is at the same time frequently possible to utilize the structural space more efficiently due to the rectangular shape.

Besides, the gas connection between the treatment apparatus and the external functional means may advantageously take place in substantially the same direction of displacement and pressing as the installation and pressing of the entire external functional means between a door-side pressing structure of the treatment apparatus and a body-side pressing structure of the treatment apparatus. It is thus possible in an economical manner to utilize both of the named functions in parallel, due to displacement and/or force of the pressing means or pressing structures of the treatment apparatus. A separate handling operation for the gas connection of the external functional means may advantageously be omitted. Due to a rigid and equidirectional parallelity of the pressing and connecting processes, demands as regards narrow or strict tolerances between the external functional means and the treatment apparatus and between single components of the treatment apparatus, which would be necessary if the gas connection were realized through a separate moving and pressing means in a spatial direction different from the one of general pressing of the external functional means, may moreover advantageously be omitted.

Advantageously, the gas connector arrangement provided in accordance with the invention may at the same time be adapted to be space-saving, low-cost, functionally safe, sturdy, and user-friendly.

As the number of functional groups may be reduced by the present invention, it may advantageously be possible to save costs, inter alia, with respect to manufacture, storage, logistics, and assembly. Furthermore, the present invention allows a reduction of demands with regard to accuracy among the single functional groups, which may advantageously further contribute to reducing costs.

Handling of the single-use functional means during mounting and removal thereof may advantageously be facilitated and become safer due to the present device.

Due to the omission of high demands with regard to rigidity, accuracy, materials and/or manufacturing processes during manufacture of the components of the external functional means such as fluid connector, support structures, drainage structures, membranes, filter membranes and membrane mounts and/or seals, clear reductions of the costs for manufacturing the external functional means may advantageously be achieved with concurrently enhanced functional reliability.

In particular, the systemically force-regulated and/or play-free coupling of the filter membrane to its drainage or support structures on either side thereof may represent a particularly valuable feature of the arrangement of the invention. The filter membrane may be clearly more resistant to strain and functionally safer than conventional arrangements.

While the filter membrane in conventional systems generally has to be made round for reasons of mechanical strength of the surrounding supporting construction and has to be fitted into the housing environment at low lateral tolerances, the filter membrane in the device of the invention may be manufactured as a rectangle from a filter membrane without cutting losses and may be welded, bonded or pressed onto the wall of the fluid supply chamber with ample lateral tolerances.

In contrast to many conventional arrangements of external functional means, mounting and support of the second drainage or support structure may in accordance with the invention be solved satisfactorily. The second support structure may advantageously be mounted in front of the filter membrane surface in an accurate manner, having sufficient rigidity and sufficient transmission of pressing force, and at the same time having drainage capability.

As the invention allows deliberately doing away with accuracy and rigidity in the second support structure, it is advantageously possible to further save costs.

In contrast with welded connections between connection mates that are of a same type or melted on both sides, which would result in the same sealing effect between the support structures and the filter membrane but would be accompanied by a lower mechanical susceptibility of the connection to strain, the selection of a low-melting point material for the fluid supply chamber in accordance with the invention allows a sealing connection which may at the same time well be subjected to mechanical strains. In this way, it is advantageously possible to avoid the first support layer becoming thinner due to melting and pressing. Furthermore it is advantageously possible to avoid material faults and/or unfavorable discontinuities of cross-section at the interfaces to the non-molten regions of the filter membrane.

Good accessibility of the filter membrane from a lateral direction in the plane of the filter membrane, is moreover possible with the second support structure provided in accordance with the invention. This may be a particular advantage in the event of inadvertent wetting of the filter membrane with liquid.

The higher drainage capability towards the interior of the fluid reception chamber may advantageously result in important safety advantages: In conventional filter membrane arrangements when filter membranes are arranged in parallel with the surface of the liquid, a pressure shock may occur in the event of inadmissible complete flooding up to the filter membrane, which may lead both to a destruction of the filter membrane and interference with other components of the external functional means and/or of the treatment apparatus. With the device of the invention, however, a level inadmissibly continuing to rise may sweep continuously across the filter membrane surface, so that the passage pressure may rise in a gently increasing manner and without shocks.

In addition, the arrangement of the filter means provided in accordance with the invention may advantageously endure innocuous multiple repeatability of a malfunction involving complete flooding of the fluid reception chamber, for in the present invention the liquid is under the influence of gravity capable of automatically draining again from the filter membrane into the fluid reception chamber.

It may furthermore advantageously be possible to even make use of this phenomenon by means of a corresponding evaluation or evaluation means to recognize a failure and to initiate reasonable countermeasures.

In this way, it may advantageously be possible to avoid an abortion of the treatment method on account of control errors of the treatment apparatus.

The apparatus of the invention for the sterile air supply of single-use part arrangements remedies the drawbacks of the current systems in a simple and at the same time cost-reducing manner, and apart from this gives rise to further advantages for the system environment of treatment apparatus and external functional means.

The arrangement of the invention is advantageously suited for utilization in any fluidic overall arrangements comprising components of the treatment apparatus and fluid-conducting components of the external functional means that are provided with the discussed pressing means.

The design of the usable arrangements of the external functional means is advantageously not restricted to only cassette designs having hard-part cassettes with film covers. Single-container arrangements previously not envisioned as cassette constructions may also be reconfigured in the sense of the device of the invention, so that the important feature of safely operating, sterile hydrophobic membranes may be achieved economically. In such a case, the cover member such as, for example, a film may be replaced with resilient injection-molded elements.

By suitable pressing of the device of the invention as part of an external functional means with a treatment apparatus, it is furthermore in a simple and cost-efficient manner advantageously possible to obtain not only a good support but also an optimum alignment of the filter means (unbending of the external functional means and of the support structures).

The device of the invention may advantageously possess a separate functionality for compensating tolerances and limiting forces. In this regard, it is advantageously possible to provide at least five options in parallel in a simple manner: a springily executed machine-side fluid connector (usually a rubber plug which may serve for sealing); a flat bottom of the fluid supply chamber that is resilient in the manner of a curved spring disc and has the effects of being springy both longitudinally and universally and aligning itself by the treatment apparatus (in combination with the fluid connector substantially being applied centrally, and a connection with the treatment apparatus having angular resilience); a springily resilient realization of the support structures, in a given case also in the direction of pressurized contact (for instance as a result of an undulating shape or of knobs that are capable of penetrating into a rubber mat of the treatment apparatus in a tolerance-compensating and springy manner); by way of a rubber mat locally configured under the second support structure so as to be separately resilient (e.g., with prisms or knobs); or by way of a resilient or springy structure in the body-side structure of the treatment apparatus (for instance springs or knobs).

Further features and aspects of example embodiments of the present invention are described in more detail below with reference to the appended Figures.

DETAILED DESCRIPTION

Figure 1:
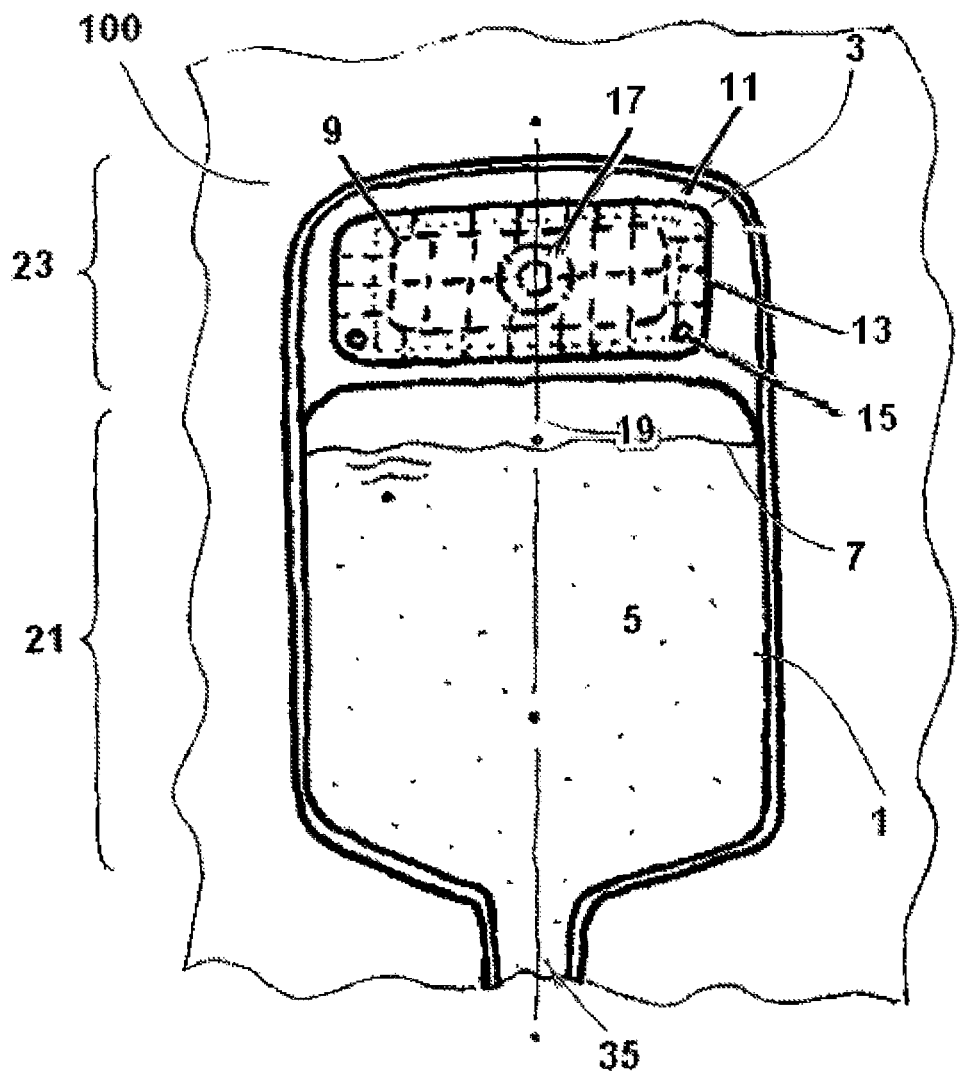
FIG. 1 is a front view of the device of the invention.

In the following, the present invention shall be described by making reference to the appended drawings. In the drawings, identical reference numerals designate same or identical elements.

FIG. 1 shows a front view of a device in accordance with an embodiment of the present invention.

The device 100 comprises a fluid reception chamber 1 as well as a fluid supply chamber 3.

In the fluid reception chamber 1 a first fluid 5 is present which is filled into the fluid reception chamber 1 up to a maximum fluid level 7.

The fluid supply chamber 3 comprises a filter means of which a filter membrane 9 as well as a first support structure 11 are shown in FIG. 1. The first support structure 11 comprises a drainage structure 13. The first support structure 11 is connected to the fluid supply chamber 3 with the aid of fixation means 15, for example rivet connections.

A fluid connector 17 is connected to a first support structure 11 of the filter means.

Through the fluid connector 17 a second fluid 19 is introduced into the fluid reception chamber 1. The second fluid may be used for treating the first fluid 5, for example by applying a pressure.

As is shown in the present FIG. 1, the fluid reception chamber 1 represents a lower region 21, and the fluid supply chamber 3 represents an upper region 23.

Figure 2:
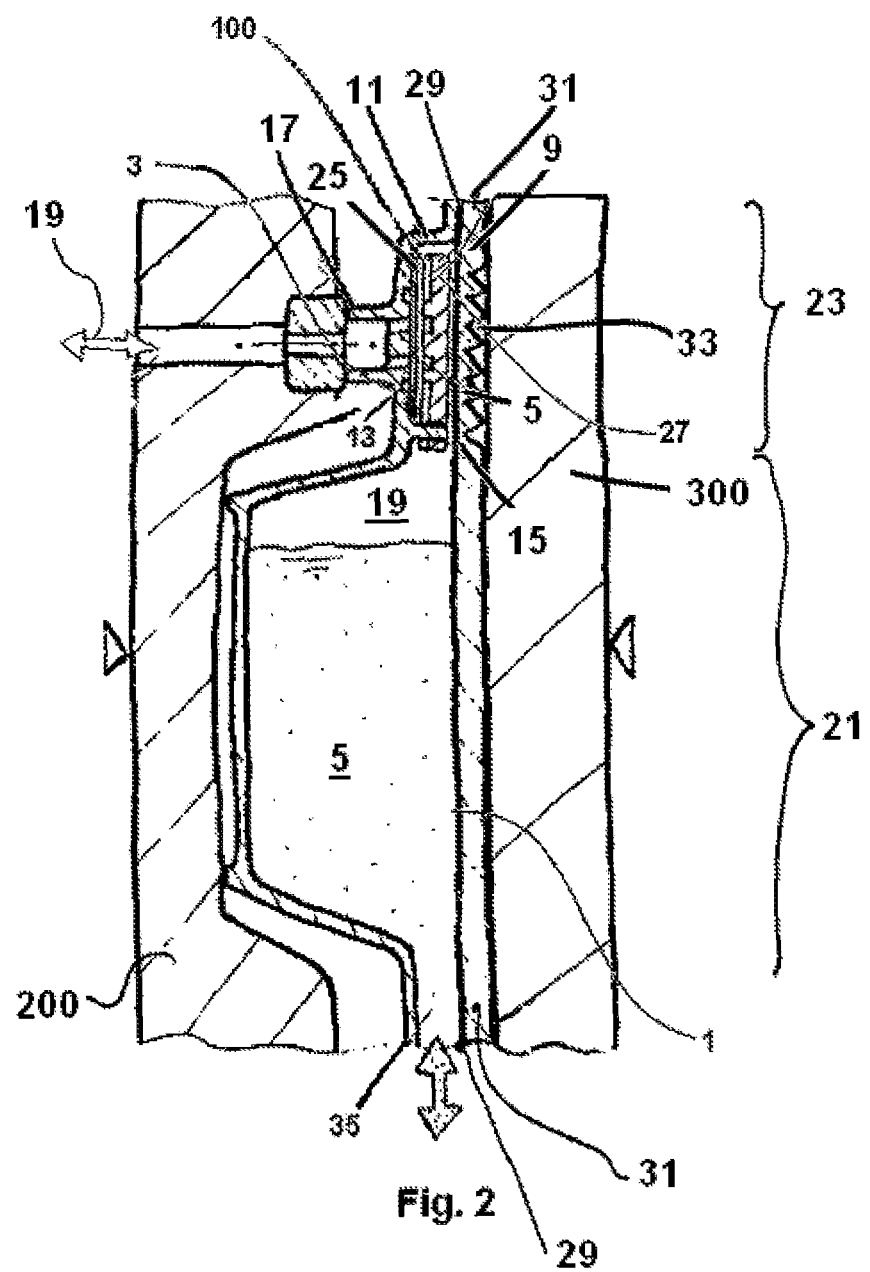
FIG. 2 is a cross-sectional view of a device of the invention.

FIG. 2 shows a device of the invention in a cross-sectional view. Here, the device 100 is represented as part of an external functional means 200 that is pressed with a treatment apparatus 300.

The lower region 21 of the device 100 forms the deeper region, i.e., the fluid reception chamber 1. The upper region 23 forms the shallower region, i.e., the fluid supply chamber 3.

As is shown by the double arrow in FIG. 2, a second fluid 19 is introduced into the fluid supply chamber 3 through a fluid connector 17.

In accordance with the representation in FIG. 2, the fluid supply chamber 3 comprises a first support structure 11 which is fastened to the fluid supply chamber 3 by means of a sealing connection 25, for example a welded or bonded connection.

On the first support structure 11 the filter membrane 9 is disposed, with the second support structure 27 in turn being provided on the latter.

The external functional means 200 is covered on one side by a cover member 29, for example a film.

Through the intermediary of a rubber mat 31 which may serve for transmitting force and/or movements through sensors or actors of the treatment apparatus 300 to the external functional means 200 or chambers and/or passages thereof, the external functional means 200 is pressed with the treatment apparatus 300.

The rubber mat 31 may have a structure 33 of specific resilience.

For the purpose of introducing or removing the fluids present inside the fluid reception chamber 1, the fluid reception chamber 1 may be provided with a fluid connection 35 at its bottom side.

Figure 3:
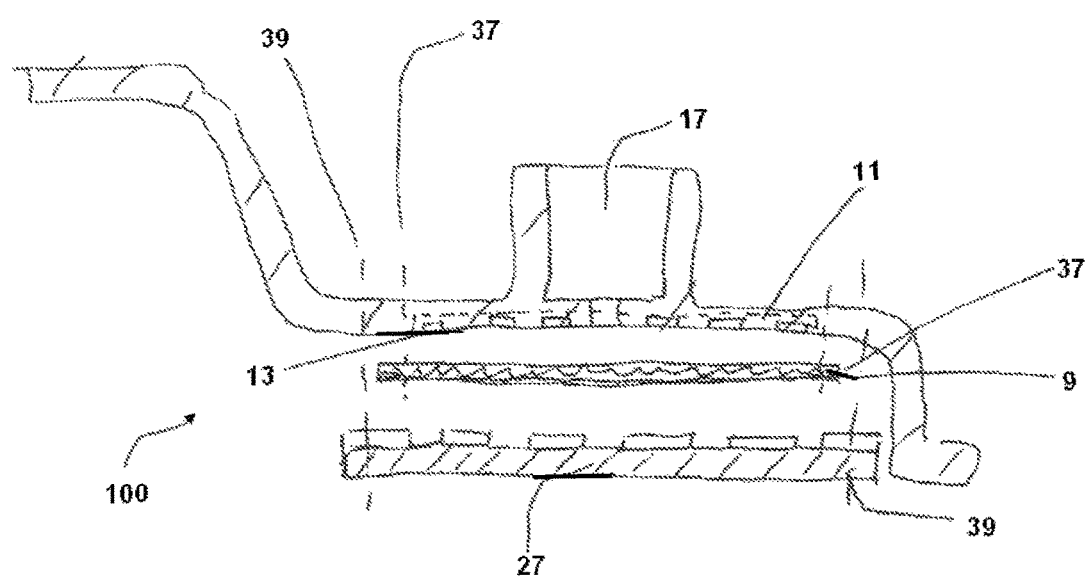
FIG. 3 is an enlarged representation of a detail of the device of the invention of FIG. 2 in a longitudinal sectional view.

FIG. 3 shows an enlarged detail or portion of the device 100 of the invention of FIG. 2, to be more precise, the filter means in a longitudinal sectional view.

In comparison with the representation of FIG. 2, the filter means was tilted by 90 degrees, so that the fluid connector 17 for the second fluid is directed upwardly in the representation of FIG. 3.

The filter membrane 9—which exemplarily comprises a membrane layer and a third support layer (not illustrated) having a woven form—is disposed between the first support structure 11 and the second support structure 27.

For a detailed description of the single components, reference is made to the above explanations.

In order to generate the sealing connection between the first support structure 11 and the filter membrane 9, a first ring zone or a first ring region 37 is provided. In order to produce the connection between the filter membrane 9 and the second support structure, a second ring zone or a second ring region 39 is provided.

The following is a List of Reference Numerals as used herein:

| Reference Numeral | Description |
| --- | --- |
| 100 | device |
| 200 | external functional means |
| 300 | treatment apparatus |
| 1 | fluid reception chamber |
| 3 | fluid supply chamber |
| 5 | first fluid |
| 7 | fluid level |
| 9 | filter membrane |
| 11 | first support structure |
| 13 | drainage structure |
| 15 | fixation means |
| 17 | fluid connector for the second fluid |
| 19 | second fluid |
| 21 | lower region |
| 23 | upper region |
| 25 | sealing connection |
| 27 | second support structure |
| 29 | cover member |
| 31 | rubber mat |
| 33 | structure of specific resilience |
| 35 | fluid port for the first fluid |
| 37 | first ring region |
| 39 | second ring region |

What is claimed is:

1. A device, comprising:
a dialysis blood treatment cassette configured to be received on a dialysis apparatus, the cassette comprising:
a hard-part;
a film cover attached to the hard-part, the hard-part and film cover cooperating to define: (i) at least one fluid supply chamber forming an upper region of the cassette and configured to supply at least one gaseous second fluid; and (ii) at least one fluid reception chamber forming a lower region of the cassette and configured to receive at least one first medical fluid through a first port or connector; and
a hydrophobic filter element disposed on an inside of the fluid supply chamber and having a filter surface through which the at least one gaseous second fluid is supplied to the fluid reception chamber through a second port or connector,
wherein all normal vectors of the filter surface of the hydrophobic filter element are not parallel to a normal vector of a fluid level of the first medical fluid present in the fluid reception chamber during use of the cassette,
wherein the first port or connector is different from the second port or connector,
wherein the first port or connector is located in the lower region of the cassette,
wherein the second port or connector is located in the upper region of the cassette,
wherein the first port or connector is configured to allow the at least one first medical fluid to enter and exit the at least one fluid reception chamber, and the second port or connector is configured to allow the at least one gaseous second fluid to enter and exit the at least one fluid reception chamber, and
wherein the first port or connector is configured so that the at least one first medical fluid enters and exits the at least one fluid reception chamber only through the first port or connector.

2. The device according to claim 1, wherein the first medical fluid is blood and the gaseous second fluid is air.

3. The device according to claim 1, wherein at least one normal vector of the filter surface of the hydrophobic filter element is substantially perpendicular to the normal vector of the fluid level.

4. The device according to claim 1, wherein all the normal vectors of the filter surface do not have a point of intersection with a fluid level of the first fluid present in the fluid reception chamber.

5. The device according to claim 1, wherein the fluid supply chamber comprises at least one fluid connector through which the second fluid is supplied to the fluid supply chamber.

6. The device according to claim 1, wherein the filter element comprises at least one filter membrane.

7. The device according to claim 6, wherein the filter membrane is rectangular.

8. The device according to claim 6, wherein the filter membrane is a sterile membrane.

9. The device according to claim 6, wherein the filter element comprises a first support structure on at least one side of the filter membrane.

10. The device according to claim 9, wherein the first support structure is disposed on the side of the filter membrane facing the interior of the fluid supply chamber.

11. The device according to claim 10, wherein the first support structure is connected in at least one outer region thereof to a connecting region of the fluid supply chamber.

12. The device according to claim 11, wherein the first support structure is connected to the fluid supply chamber by material connection.

13. The device according to claim 12, wherein the first support structure is welded with the fluid supply chamber.

14. The device according to claim 10, wherein the first support structure is at least in an outer region thereof made of a higher-melting point material than a connecting region of the fluid supply chamber.

15. The device according to claim 9, wherein a second support structure is disposed on the side of the filter membrane facing away from the interior of the fluid supply chamber.

16. The device according to claim 15, wherein the second support structure comprises the same material as the fluid supply chamber.

17. The device according to claim 15, wherein the second support structure covers the filter membrane substantially completely.

18. The device according to claim 10, wherein the first support structure and/or the second support structure comprises a drainage structure.

19. The device according to claim 18, wherein the first and second support structures comprise a drainage structure that is substantially identical in a mirror-reversed manner relative to a main plane of the filter membrane.

20. The device according to claim 1, wherein the fluid reception chamber has a first structural height, and the fluid supply chamber has a second structural height different from the first structural height.

21. The device according to claim 1, wherein the fluid supply chamber is disposed above the fluid reception chamber during use of the device.

22. The device according to claim 1, wherein the device is integrated into an external functional means by material connection.

23. The device according to claim 1, wherein the device is configured to treat the first fluid.

24. The device according to claim 1, wherein the second fluid is a gas.

25. The device according to claim 1, wherein the first fluid is a liquid.

26. The device according to claim 25, wherein the liquid is blood.

27. The device according to claim 1, wherein the cassette is a dialysis blood treatment cassette.

28. The device according to claim 27, wherein the filter element of the dialysis blood treatment cassette is arranged in parallel with the film cover.

29. The device according to claim 28, wherein the filter element is spaced apart from the film cover.

30. A treatment apparatus for treating at least one fluid, the treatment apparatus comprising the device according to claim 1.

31. The treatment apparatus according to claim 30, wherein the treatment apparatus comprises the dialysis apparatus.

32. The treatment apparatus according to claim 31, wherein the dialysis apparatus comprises at least one reception means for receiving the dialysis blood treatment cassette.

33. A treatment apparatus for treating at least one fluid, the treatment apparatus comprising the dialysis blood treatment cassette according to claim 27.

34. The treatment apparatus according to claim 33, wherein the treatment apparatus comprises a dialysis apparatus.

35. The treatment apparatus according to claim 34, wherein the dialysis apparatus comprises at least one reception means for receiving the dialysis blood treatment cassette.

* * * * *